United States Patent
Kwok et al.

(10) Patent No.: US 8,146,597 B2
(45) Date of Patent: Apr. 3, 2012

(54) NASAL MASK ASSEMBLY

(75) Inventors: Philip Rodney Kwok, Chatswood (AU);
Karthikeyan Selvarajan, Gosford (AU);
Clive Solari, Lindfield (AU)

(73) Assignee: ResMed Limited, Bella Vista (AU)

( * ) Notice: Subject to any disclaimer, the term of this patent is extended or adjusted under 35 U.S.C. 154(b) by 1050 days.

(21) Appl. No.: 12/067,432

(22) PCT Filed: Oct. 18, 2006

(86) PCT No.: PCT/AU2006/001534
§ 371 (c)(1),
(2), (4) Date: Mar. 19, 2008

(87) PCT Pub. No.: WO2007/045023
PCT Pub. Date: Apr. 26, 2007

(65) Prior Publication Data
US 2008/0230067 A1 Sep. 25, 2008

Related U.S. Application Data

(60) Provisional application No. 60/727,826, filed on Oct. 19, 2005.

(51) Int. Cl.
*A62B 18/02* (2006.01)
(52) U.S. Cl. .............................. 128/207.13; 128/206.21
(58) Field of Classification Search ............. 128/205.25, 128/206.21–207.18
See application file for complete search history.

(56) References Cited

U.S. PATENT DOCUMENTS

| 6,886,564 B2 | 5/2005 | Sullivan et al. |
| 2003/0145857 A1 | 8/2003 | Sullivan et al. |
| 2003/0145859 A1 | 8/2003 | Bohn et al. |
| 2003/0172936 A1* | 9/2003 | Wilkie et al. ............ 128/207.18 |
| 2006/0060200 A1* | 3/2006 | Ho et al. .................. 128/206.24 |
| 2006/0081251 A1* | 4/2006 | Hernandez et al. ...... 128/206.21 |

FOREIGN PATENT DOCUMENTS

| EP | 1 057 494 | 11/2004 |
| WO | WO 98/18514 | 5/1998 |
| WO | WO 01/32250 | 5/2001 |
| WO | WO 01/97892 | 12/2001 |
| WO | WO 2004/012803 | 2/2004 |

OTHER PUBLICATIONS

International Search Report for PCT/AU2006/001534 mailed Jan. 24, 2007.
Written Opinion of the International Searching Authority for PCT/AU2006/001534.

* cited by examiner

*Primary Examiner* — Justine Yu
*Assistant Examiner* — Rachel Young
(74) *Attorney, Agent, or Firm* — Nixon & Vanderhye P.C.

(57) ABSTRACT

A nasal mask assembly includes a relatively flexible cushion arrangement including a cushion that provides a breathing chamber and a face-contacting portion to form a seal around the patient's nose in use, an inlet tube supported by the cushion to deliver breathable gas into the breathing chamber for breathing by the patient, and three support members extending outwardly from the cushion. A relatively rigid frame is provided to a front side of the cushion arrangement. The frame includes three headgear attachment structures. Headgear includes three headgear straps engagable with the three support members and the three headgear attachment structures to maintain the cushion arrangement in a desired position on the patient's face.

21 Claims, 13 Drawing Sheets

NASAL MASK ASSEMBLY

CROSS REFERENCE TO PRIORITY APPLICATION

This application is the U.S. national phase of International Application No. PCT/AU2006/001534 filed 18 Oct. 2006 which designated the U.S. and claims the benefit of U.S. Provisional Application No. 60/727,826, filed Oct. 19, 2005, the entire contents of each of which are incorporated herein by reference in its entirety.

FIELD OF THE INVENTION

The present invention relates to a nasal mask assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

Patient interfaces, such as a nasal mask assembly, for use with blowers and flow generators in the treatment of sleep disordered breathing (SDB) typically include a soft-patient contacting portion, such as a cushion, and a rigid shell or frame. In use, the patient interface is held in a sealing position by headgear so as to enable a supply of air at positive pressure to be delivered to the patient's airways.

A key factor in the efficacy of therapy and compliance of patients with therapy is the comfort and fit of the patient interface. While there are a large number of patient interfaces designed for adults, there are relatively few designed to suit infants.

SUMMARY OF THE INVENTION

One aspect of the present invention relates to a nasal mask assembly suitable for infants.

Another aspect of the present invention relates to a nasal mask assembly including a relatively flexible cushion arrangement including a cushion that provides a breathing chamber and a face-contacting portion to form a seal around the patient's nose in use, an inlet tube supported by the cushion to deliver breathable gas into the breathing chamber for breathing by the patient, and three support members extending outwardly from the cushion. A relatively rigid frame is provided to a front side of the cushion arrangement. The frame includes three headgear attachment structures. Headgear includes three headgear straps engagable with the three support members and the three headgear attachment structures to maintain the cushion arrangement in a desired position on the patient's face.

Another aspect of the present invention relates to a nasal mask assembly including a relatively flexible cushion that provides a breathing chamber and a face-contacting portion to form a seal around the patient's nose in use. A relatively rigid frame is attached to the cushion through the breathing chamber. The frame includes a plurality of attachment pins that protrude through the cushion. Headgear includes headgear straps engagable with respective attachment pins of the frame to maintain the cushion in a desired position on the patient's face.

Another aspect of the present invention relates to a nasal mask assembly including a relatively flexible cushion that provides a breathing chamber and a face-contacting portion to form a seal around the patient's nose in use. A relatively rigid frame is attached to a front side of the cushion. The frame includes a plurality of recesses. Headgear includes headgear straps provided with attachment pins that are engagable with respective recesses of the frame to maintain the cushion in a desired position on the patient's face.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following includes descriptions of nasal mask assemblies according to several illustrated embodiments of the present invention. In each of the illustrated embodiments, the nasal mask assembly includes a cushion arrangement and a frame that provide engagement and/or attachment points for headgear. The cushion arrangement provides a seal around the patient's nose to enable the delivery of breathable gas to the patient's nose in use. Moreover, the cushion arrangement and frame are structured to distribute forces from the headgear to various regions of the patient's face.

In an embodiment, the nasal mask assembly is sized and/or shaped to accommodate features of an infant, e.g., in the range of 6-18 months. However, aspects of the present invention may be applicable to other breathing arrangements, e.g., full-face, and other age groups. Also, each illustrated embodiment includes features that may be used with and/or in the other illustrated embodiments, as would be apparent to those of ordinary skill in the art.

1. First Embodiment of Nasal Mask Assembly

Figure 1:
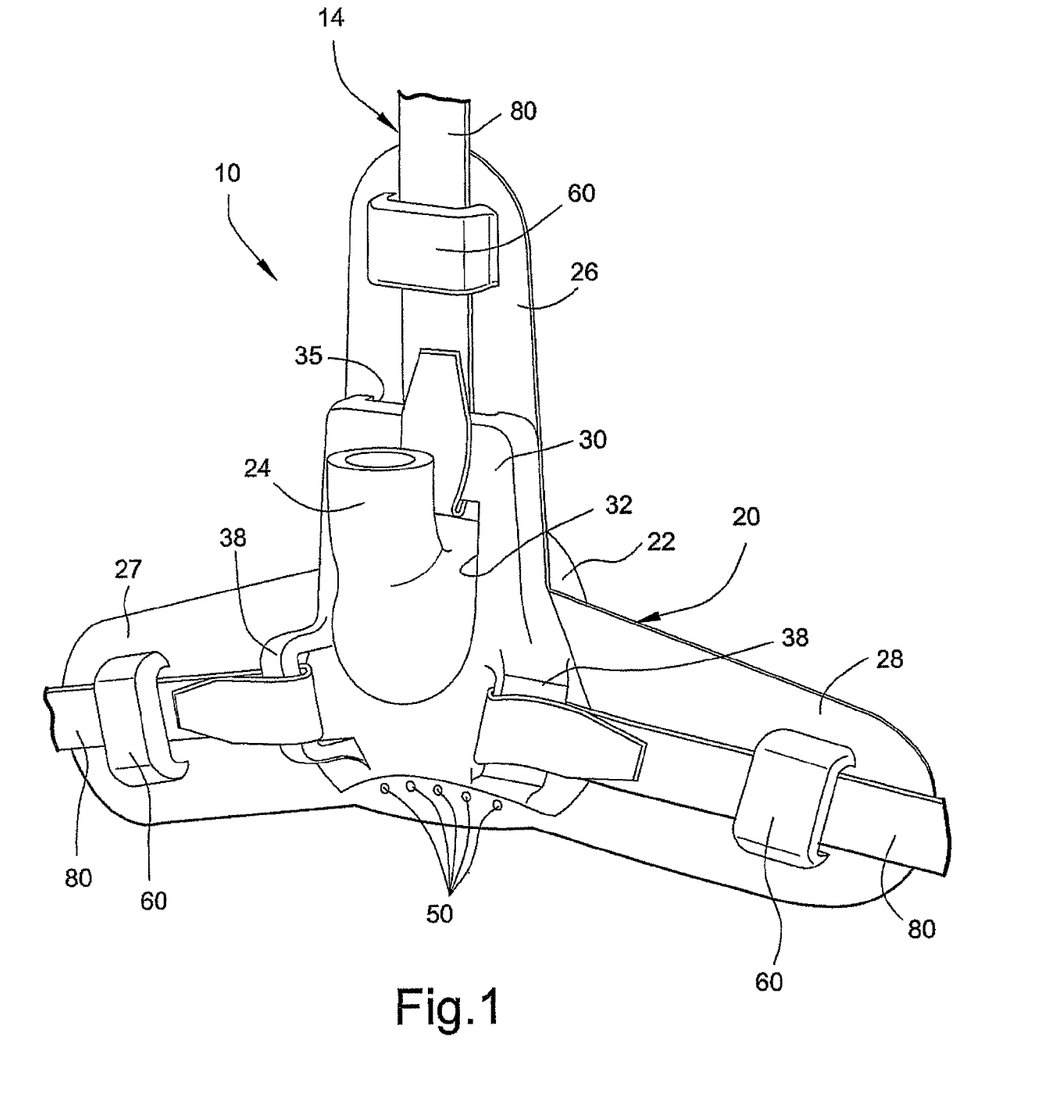
FIG. 1 is a front perspective view of a nasal mask assembly according to an embodiment of the present invention.
Figure 2:
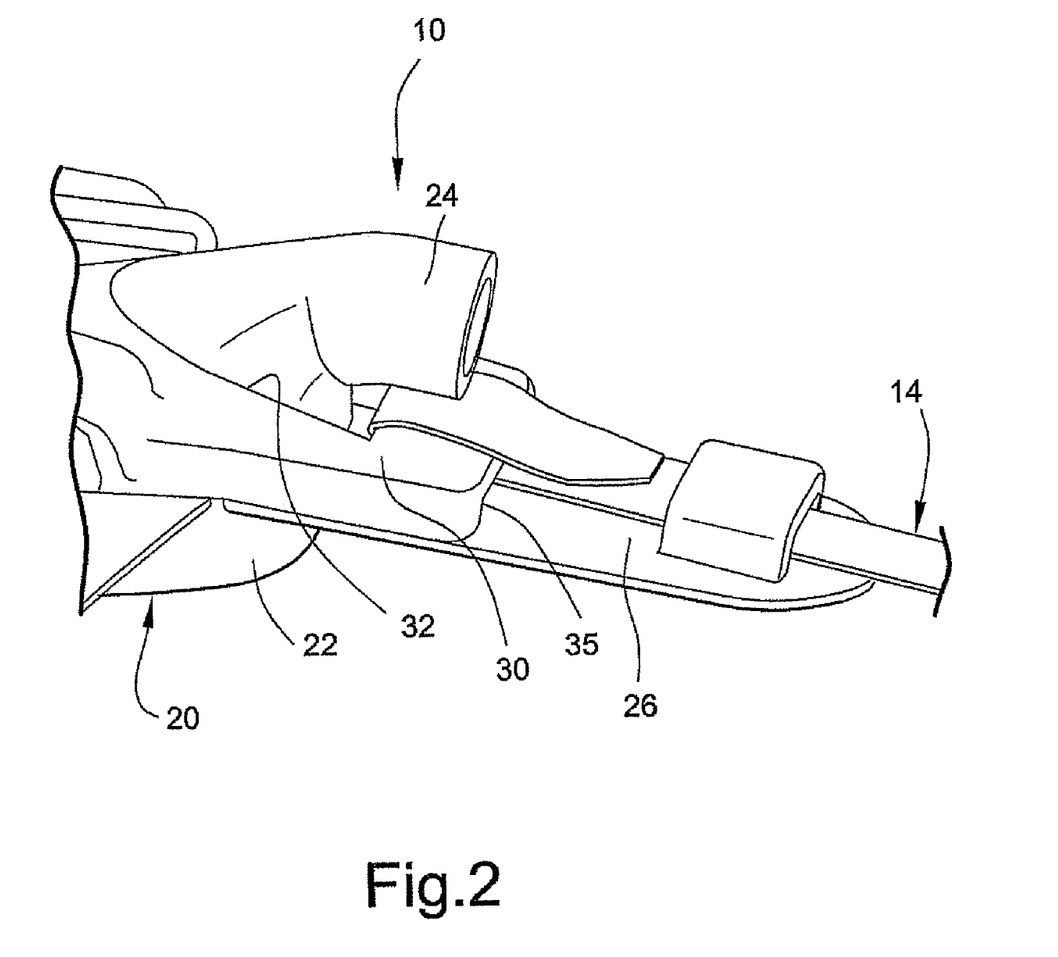
FIG. 2 is a partial side perspective view of the nasal mask assembly shown in FIG. 1.

FIGS. 1 and 2 illustrate a nasal mask assembly 10 according to an embodiment of the present invention. As illustrated, the nasal mask assembly 10 includes a cushion arrangement 20 that provides an effective seal around the patient's nose and a frame 30 provided to the cushion arrangement 20. Headgear 14 is engagable with the cushion arrangement 20 and the frame 30 so as to maintain the cushion arrangement 20 in a desired position on the patient's face.

1.1 Cushion Arrangement

Figure 3:
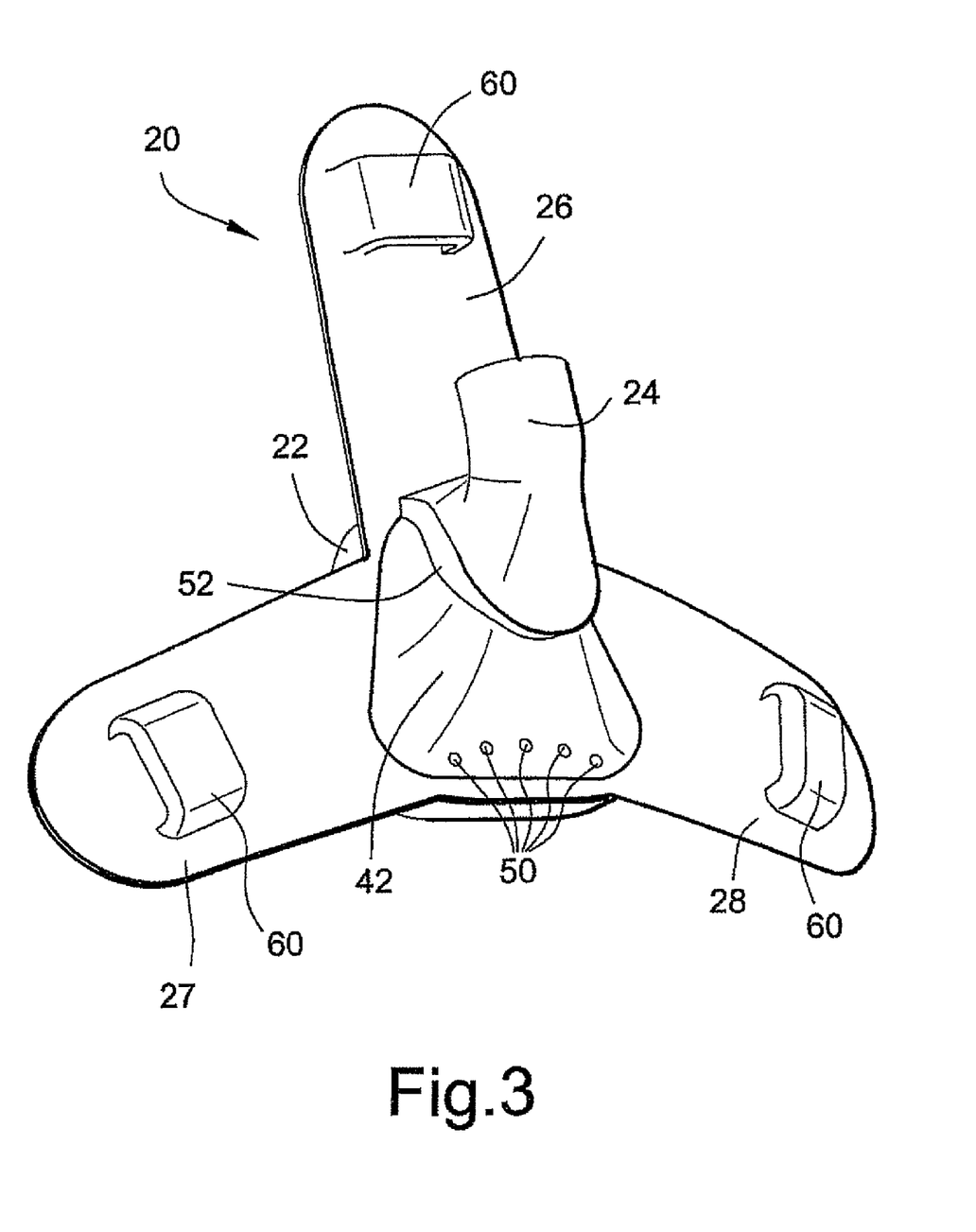
FIG. 3 is a front perspective view of a cushion arrangement of the nasal mask assembly shown in FIG. 1.
Figure 4:
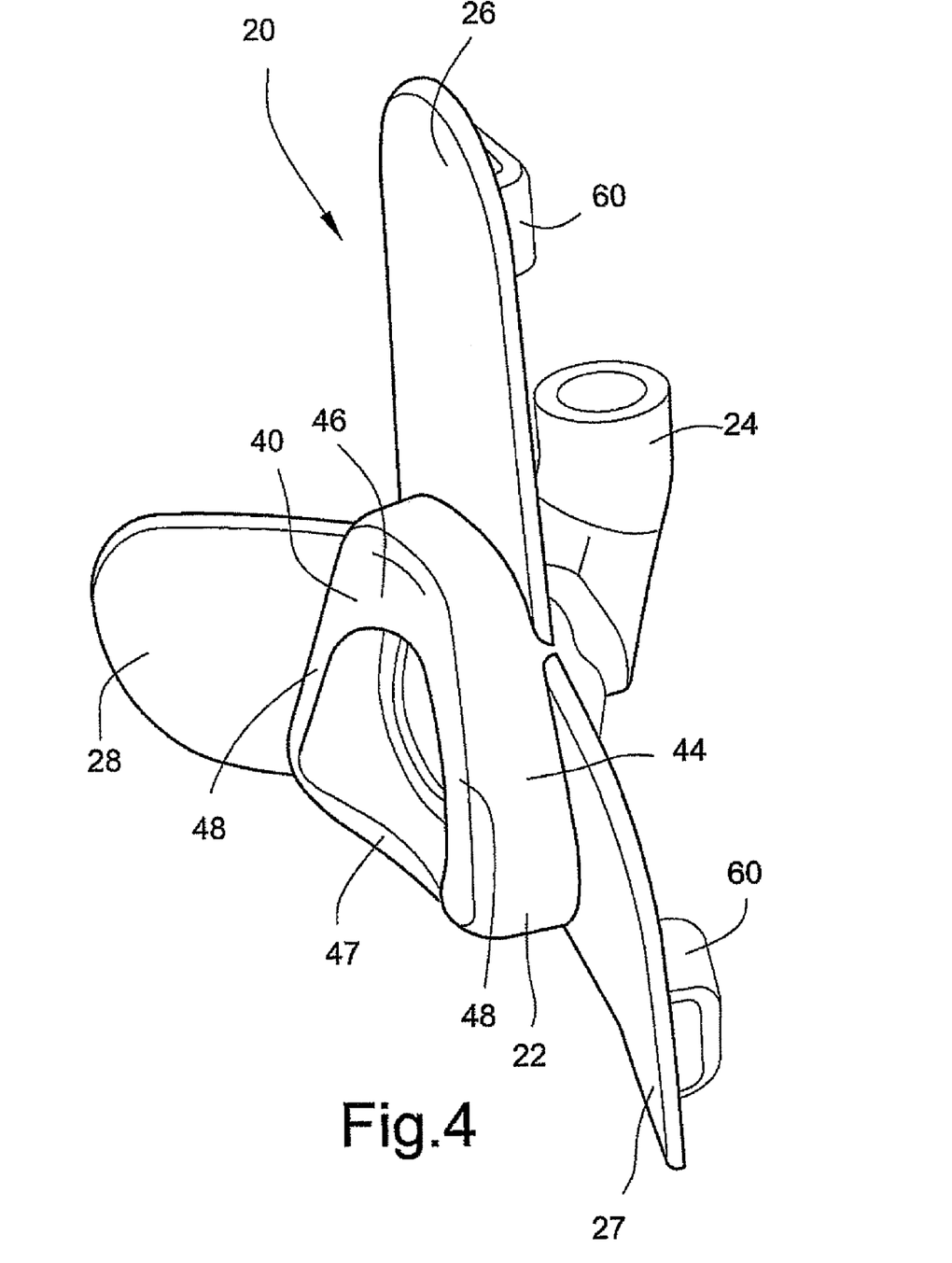
FIG. 4 is a side perspective view of the cushion arrangement shown in FIG. 3.
Figure 5:
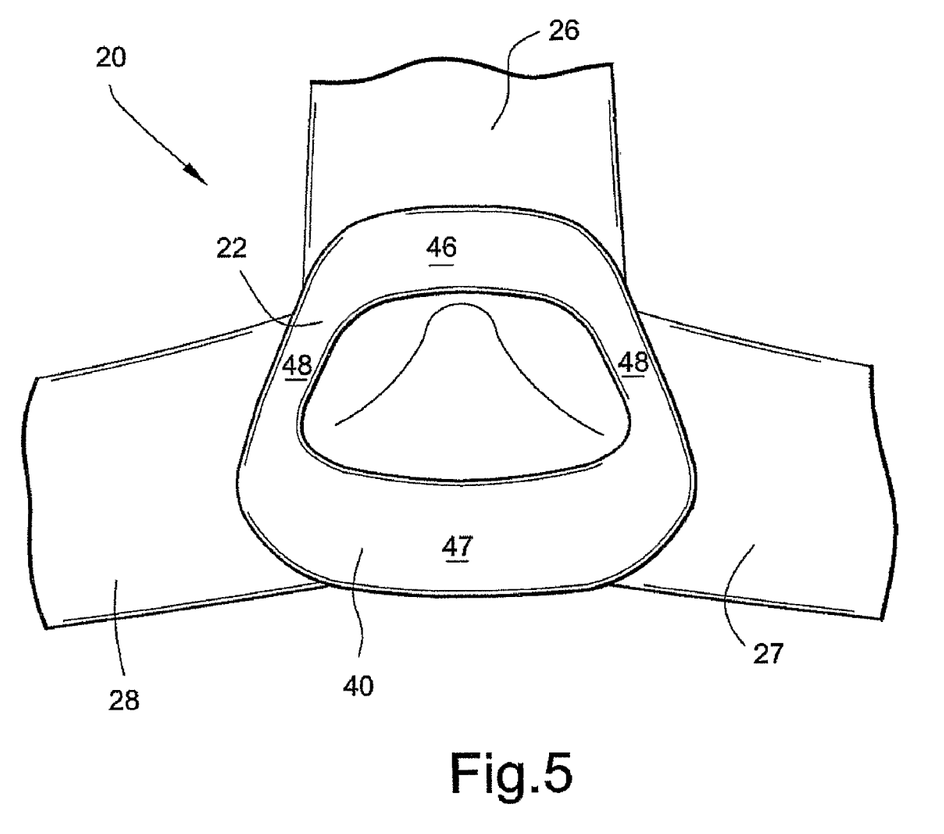
FIG. 5 is a partial rear view of the cushion arrangement shown in FIG. 3.

As best shown in FIGS. 3-5, the cushion arrangement 20 includes a cushion 22 that defines an air chamber, an inlet tube 24 supported by the cushion 22 to deliver breathable gas into the cushion 22 for breathing by the patient, and three support members or limbs 26, 27, 28 extending outwardly from the cushion 22. The cushion arrangement 20 is formed of a flexible elastomeric or plastic material, e.g., silicone. In the illustrated embodiment, the cushion 22, the inlet tube 24, and the support members 26, 27, 28 are formed as a one-piece structure such that the cushion 22, the inlet tube 24, and the support members 26, 27, 28 are integrally formed in one-piece, e.g., by silicone in an injection molding process. However, the cushion 22, the inlet tube 24, and the support members 26, 27, 28 may be formed separately from one another, e.g., by silicone in an injection molding process, and then attached to one another.

1.1.1 Cushion

The cushion 22 includes a face contacting portion 40 adapted to form a seal around the patient' nose in use, and front and side walls 42, 44 that define an air chamber. In the illustrated embodiment, the face contacting portion 40 has a single wall construction, e.g., membrane only, that defines a general c-shaped contour in cross-section. However, the face contacting portion 40 may have a multi-wall construction, e.g., membrane and underlying support cushion.

The face contacting portion 40 is relatively thin, e.g., thickness in the range of 0.2-0.3 mm (e.g., 0.23 mm), which makes the face contacting portion 40 squashable or easily deformable. Also, the single wall construction of the face contacting portion 40 provides a shallow cushion with a short profile to reduce the perceived bulk of the cushion and to best accommodate an infant's less prominent bridge.

As best shown in FIG. 5, the cushion 22 has a rounded or circular trapezoidal shape. That is, the cushion 22 is contoured to avoid straight lines that provide sharp or cutting edges. This arrangement prevents discomfort due to contact with sharp or cutting edges. The nasal bridge region 46 of the cushion 22 is relatively wide to accommodate a wide range of facial shapes. Also, the upper lip region 47 of the cushion 22 provides less curvature than that provided by the nasal bridge region 46 of the cushion 22.

As best shown in FIGS. 4 and 5, the side walls 44 and face contacting portion 40 along the cheek regions 48 of the cushion 22 have substantially flat contouring along its length. This arrangement more closely follows the contours of an infant's cheeks, for example.

One or more vents 50 may be provided in the front wall 42 of the cushion 22 for $CO_2$ washout. As shown in FIG. 1, the bottom of the frame 30 is contoured around the vents 50. However, other vent arrangements are possible. For example, the cushion may include a large opening that is adapted to receive a vent insert. In another embodiment, the cushion may include a large opening that is covered by the frame which includes one or more smaller vent openings or a vent insert.

1.1.2 Inlet Tube

The inlet tube 24 extends from the cushion 22 and is adapted to be connected to an air delivery tube that delivers breathable gas into the cushion 22 for breathing by the patient. As illustrated, the inlet tube 24 is extends or curves upwardly so that the air delivery tube passes over the top of the patients head in use.

In an embodiment, the inlet tube 24 may have an inside diameter of about 8 mm. The relatively smaller inlet tube 24 provides air pressure at a level suitable for infants. The inlet tube 24 may be communicated with a larger bore tube, e.g., 15 or 22 mm inside diameter, associated with the flow generator.

As illustrated, the inlet tube 24 defines a shoulder 52 that facilitates alignment and positioning of the frame 30 on the cushion arrangement 20.

1.1.3 Support Members

The support members or limbs 26, 27, 28 extend outwardly from the cushion 22 and provide engagement points for engaging headgear straps 80 of the headgear 14. In use, the support members 26, 27, 28 support the cushion arrangement on the patient's face and distribute forces from the headgear straps 80 to the cheeks and forehead of the patient.

As illustrated, the support members 26, 27, 28 are arranged in a triangular or inverse-Y-shape configuration so that, in use, the support member 26 extends over the patient's forehead and the support members 27, 28 extend over the patient's cheeks. The support members, 26, 27, 28 e.g., formed of silicone, are relatively flexible which allows the support members 26, 27, 28 to bend or flex and match the contour of the patient's face in use.

Each support member 26, 27, 28 includes a loop or anchor 60, e.g., formed of silicone, that retains a respective strap 80 of the headgear. Specifically, each loop 60 is arranged to receive a strap 80 of the headgear therethrough so as to align the strap 80 with the respective support member 26, 27, 28 and the attachment points provided on the frame 30.

The function of the support members 26, 27, 28 is to evenly distribute the force of the cushion 22 around the patient's face. Specifically, when mask assembly 10 is placed on the patient's face, e.g., infant's face, the relatively thin cushion 22 is deformed onto the nasal area of the patient's face and the support members 26, 27, 29 are moved into contact with the forehead and cheek regions of the patient's face. Thus, forces from the headgear straps are distributed evenly to the cushion 22 and distributed to forehead and cheek regions of the patient's face.

In addition, the headgear straps 80 pass over the silicone support members 26, 27, 28 so that the headgear straps 80 do not contact patient's face in use. Therefore, the headgear straps 80 do not cause chafing, e.g., during strap adjustment.

In an embodiment, the support members may be formed separately from the cushion and detachably mounted thereto.

1.2 Frame

Figure 6:
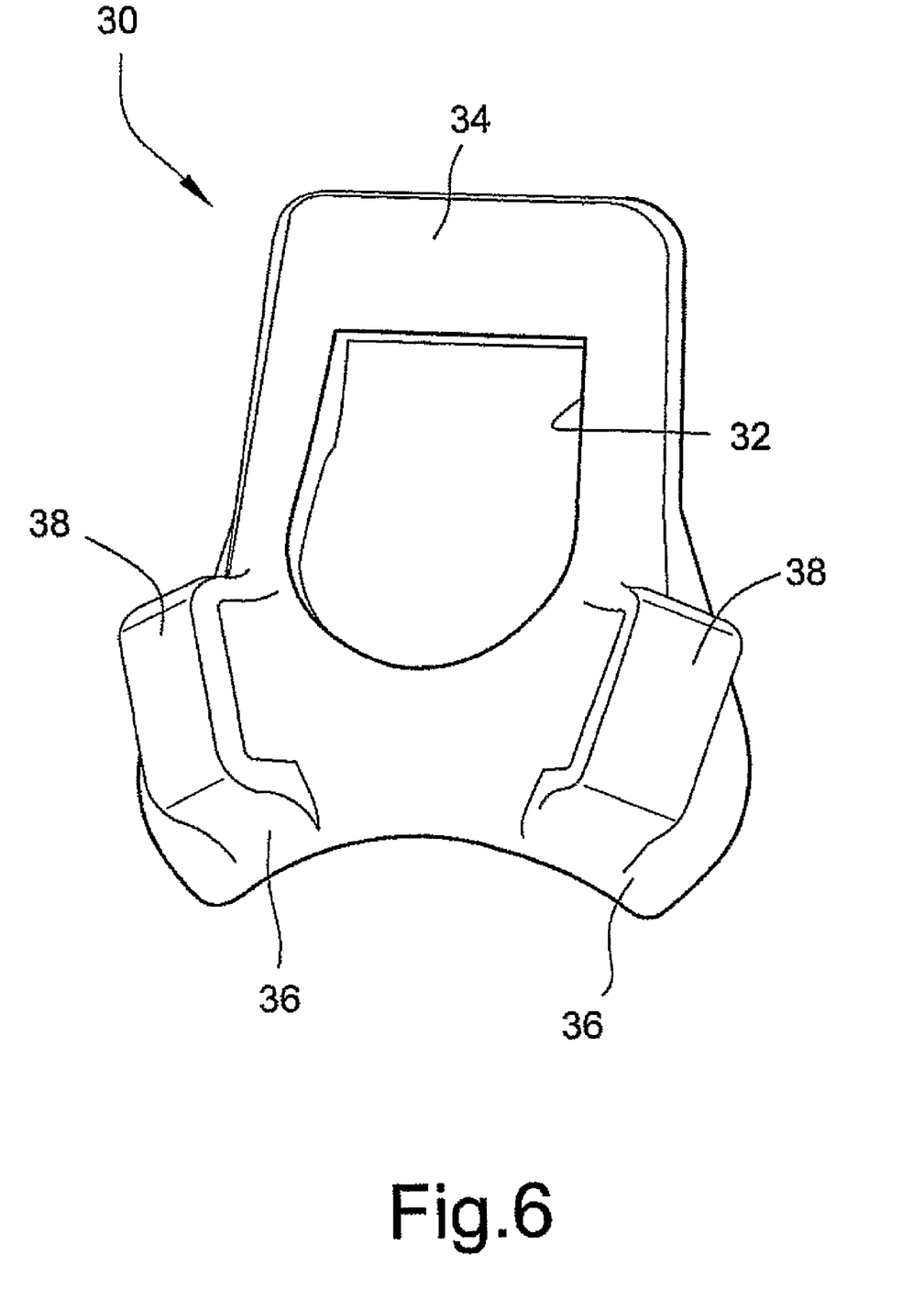
FIG. 6 is a front perspective view of a frame of the nasal mask assembly shown in FIG. 1.
Figure 7:
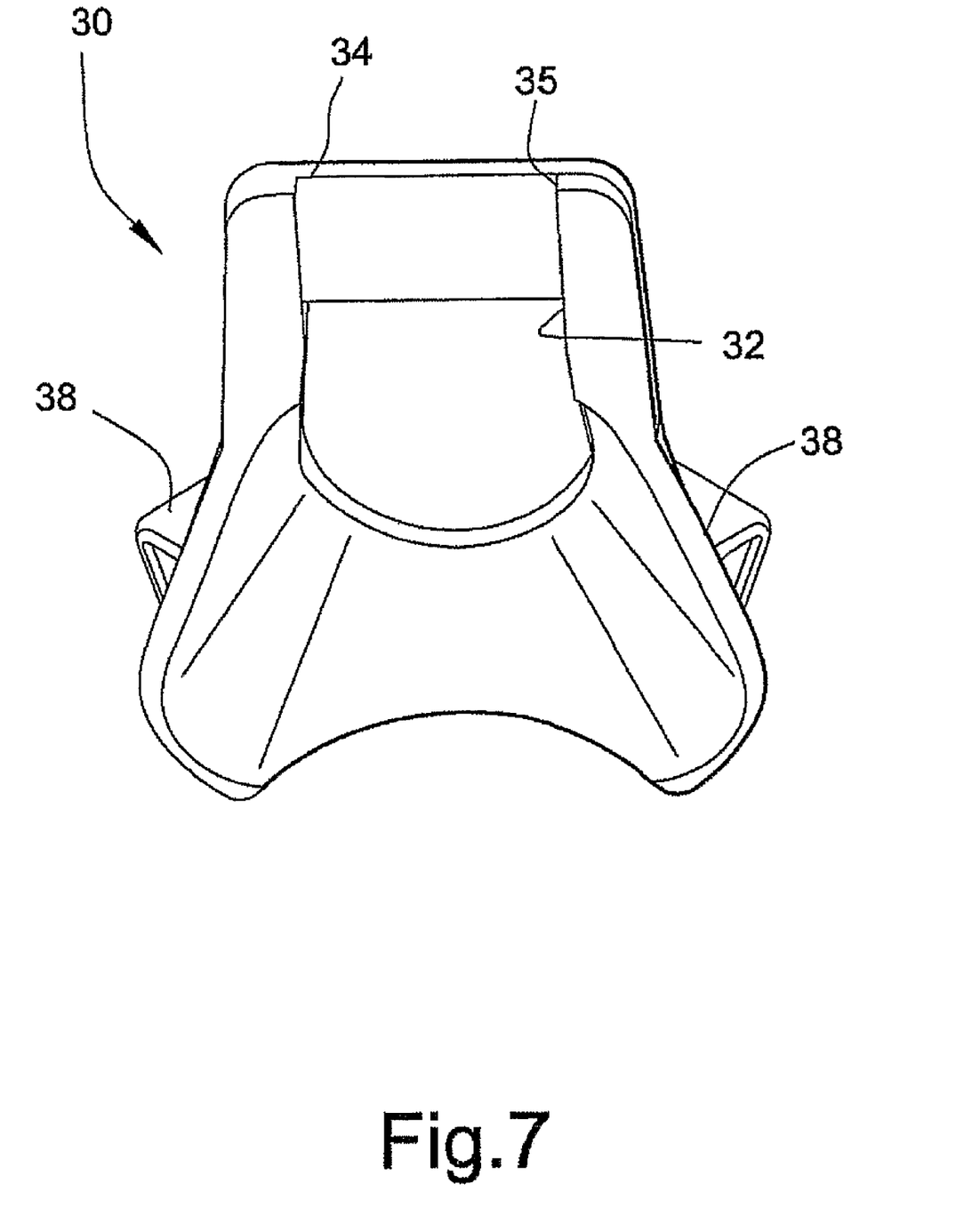
FIG. 7 is a rear perspective view of the frame shown in FIG. 6.

As best shown in FIGS. 6 and 7, the frame or shell 30 is provided to the front of the cushion arrangement 20 and provides attachment points for attaching the headgear straps 80 of the headgear. The frame 30 provides a stable connection between the headgear straps 80 and the cushion arrangement 20 in order to secure the cushion arrangement 20 at the correct orientation on the patient's face.

The frame 30 is a relatively rigid element that is constructed from a rigid or semi-rigid material. In the illustrated embodiment, the frame 30 is manufactured of a relatively rigid or stiff plastic or metal material. However, other materials of greater or less rigidity are also possible.

The frame 30 includes a central opening 32 that receives the inlet tube 24 therethrough when attached to the front wall 42 of the cushion 22. The edges of the opening 32 engage the shoulder 52 of the inlet tube 24 to align and position the frame 30 on the cushion arrangement 20. The frame 30 may be retained to the cushion arrangement 20 in any suitable manner, e.g., friction fit, adhesive, etc.

In the illustrated embodiment, the frame 30 provides three rigid attachment points for attaching the headgear straps of headgear. Specifically, the upper portion 34 of the frame 30 includes a recess 35 and each side portion 36 of the frame 30 includes a loop or anchor 38. In use, one headgear strap 80 may be passed through the upper most loop 60 of cushion arrangement 20 to the recess 35 and wrapped around the upper portion 34, and the other headgear straps 80 may be passed through lateral loops 60 of cushion arrangement 20 and wrapped around respective anchors 38 (see FIGS. 1 and 2).

Fastening of the headgear straps 80 may be provided by a hook and loop material, e.g., Velcro®. However, other fastening arrangements are possible. For example, the upper portion 34 and anchors 38 may each include a pin. In use, a headgear strap with a series of holes along its length may be wrapped around the respective upper portion 34/anchors 28, and the pin may be inserted through a hole of the strap to fasten the strap in place.

The frame 30 allows the headgear straps 80 to be looped and fastened at the front of the patient's face so that one can easily adjust the headgear straps 80 at the front of the patient's face (rather than at the sides of the patient's face). This arrangement allows adjustment regardless of the position of patient's face, e.g., one can adjust the straps 80 even if patient is sleeping on his/her side.

As best shown in FIG. 1, the bottom of the frame 30 is contoured or cut-out to avoid contact with the patient's face and to allow for the vents 50 in the cushion 22.

1.3 Infant Use of Nasal Mask Assembly

The nasal mask assembly 10 includes several features that facilitate use for infants. For example, the nasal mask assembly 10 is structured such that only the silicone cushion 22 and support members 26, 27, 28 contact the infant's face in use. That is, the silicone support members 26, 27, 28 are provided between the headgear straps 80 and the infant's face in use so that the headgear straps 80 do not contact the infant's face. This arrangement provides comfort and doesn't allow the more rough or coarse material of headgear straps 80 to cause chafing on the infant's face.

Another feature is the triangular arrangement of the support members 26, 27, 28 and the rounded trapezoidal cushion shape. This provides distribution of headgear forces around various regions of an infant's face.

Another feature is the headgear attachment points at the front of the infant's face. This allows easy configuration or adjustment of the headgear straps 80 regardless of the infant's sleeping position.

Still another feature is the contours of the cushion 22 to accommodate features of an infant.

In addition, the smaller bore inlet tube, e.g., 8 mm vs. larger 15 or 22 mm provided in known masks, provides air pressure at a level suitable for infants.

1.4 Alternative Frame Embodiments

In the illustrated embodiment, the nasal mask assembly 10 includes a common cushion 22 (although there may be several sizes), and a relatively rigid frame 30 that may be interchangeable depending on application. In another embodiment, the nasal mask assembly may include a common cushion (although there may be several sizes), and a deformable or malleable frame.

Typically, the purpose of the frame is to support the cushion and hold and support the headgear straps. In one embodiment of the invention, the purpose of the frame 30 is to define the seal. This may occur via changing the shape of the underlying cushion or membrane, changing the force of the seal on various regions of the patient's face, and/or changing the stiffness of the seal on various regions of the patient's face.

One purpose is to provide a better fit to the patient (custom fit). Another purpose is to vary the sealing pressure or cushion stiffness on the patient's face according to comfort or seal at various regions around the cushion. A further purpose may be to provide different sealing pressure or cushion stiffness on the patient at different times (changing nightly, weekly, monthly or as the patient grows). One advantage is to prevent deformation in the younger patient due to continual nightly pressure at the same points. A further advantage is to allow periodic adjustment of the shape or pressure of the seal as the patient's face grows.

The change in shape, size or pressure applied by the frame 30 may be achieved by changing the entire frame or having a malleable frame. A malleable frame may be achieved by the use of different materials (rigid, semi-rigid, and/or flexible). Materials may include silicone, deformable plastics such as polycarbonate, semi-rigid polyurethane, memory materials or metal inserts (e.g., copper or aluminum). A malleable frame may also be achieved by the use of varying material thicknesses.

In one embodiment, cut-outs of a frame or partial frames may be used to remove pressure on a region of a patient's face and a flexible or ballooning membrane may be used at this point (e.g., nasal region).

Figure 8:
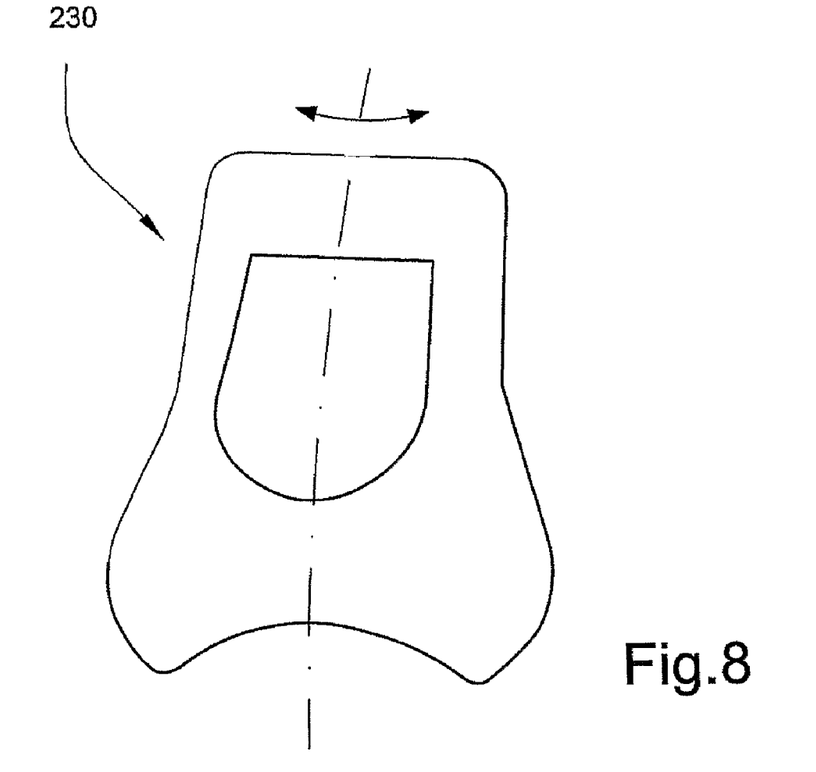
FIG. 8 is a front schematic view of an embodiment of a bendable frame for a nasal mask assembly.
Figure 9:
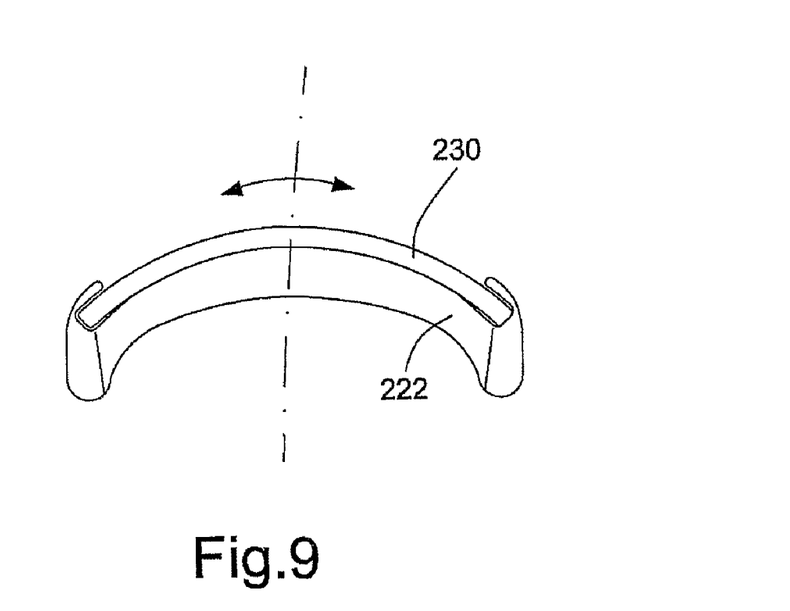
FIG. 9 is a top schematic view of the bendable frame shown in FIG. 8 attached to a cushion.

FIGS. 8-9 show a malleable or bendable frame 230 that bends around the face of a patient to help define the seal (FIG. 9 shows the frame 230 attached to a flexible cushion and/or membrane 222). As illustrated, the frame 230 is flexible in one direction but rigid in another. This frame 230 stops the cushion 222 from collapsing and forms the cushion 222 around the patient's face (similar to a hinging effect). This type of single axis deformation is particularly suited to infants since they typically have similar facial shapes that are relatively flat.

Figure 10:
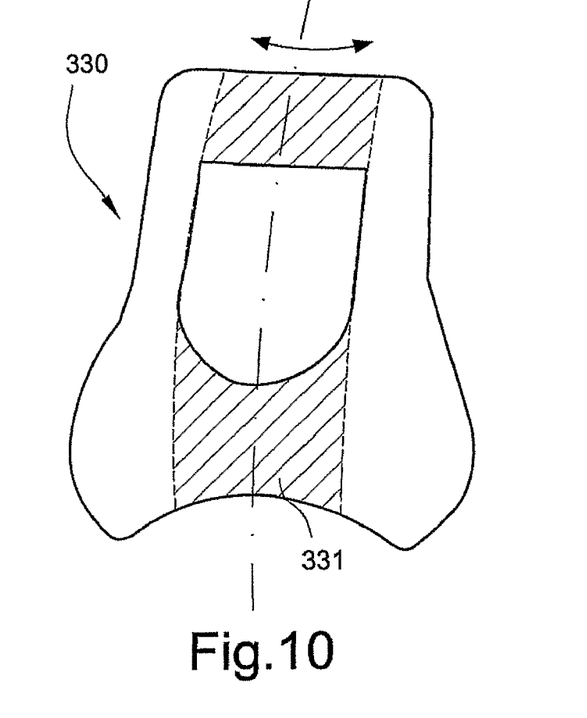
FIG. 10 is a front schematic view of another embodiment of a bendable frame for a nasal mask assembly, the bendable frame constructed from two materials with a central bendable section.

FIG. 10 shows a frame 330 made from two materials with a central malleable section 331. To assemble, the frame 330 may slide over or within the cushion. The frame 330 may be completely deformable and could be used to create a custom seal around the face of a particular patient.

Figure 11:
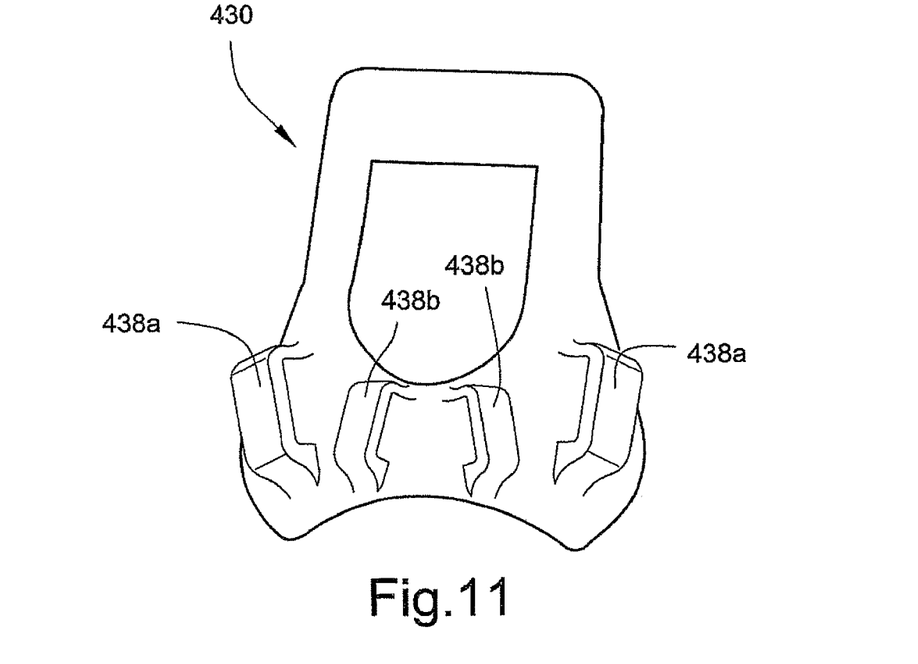
FIG. 11 is a front schematic view of an embodiment of a frame for a nasal mask assembly showing alternative headgear strap attachment locations.

In an alternative embodiment, the pressure on the seal can be influenced by strap location. FIG. 11 shows a frame 430 offering alternative headgear strap attachment locations 438a and 438b. One location may be chosen for continual use in order to enhance the seal or fit to a particular patient. Alternatively, the location may be changed periodically in order to vary the pressure points on a patient and help prevent the resultant facial deformation as the patient grows. In one embodiment, the attachment locations may remain in a fixed location but change height, thus changing the leverage applied to the face by the headgear.

In another embodiment, the frame may be Y-shaped with headgear attachment points provided on each arm. In yet another embodiment, the frame could be a wire-type frame that is bendable to match the contour of a patient's face.

2. Second Embodiment of Nasal Mask Assembly

Figure 12:
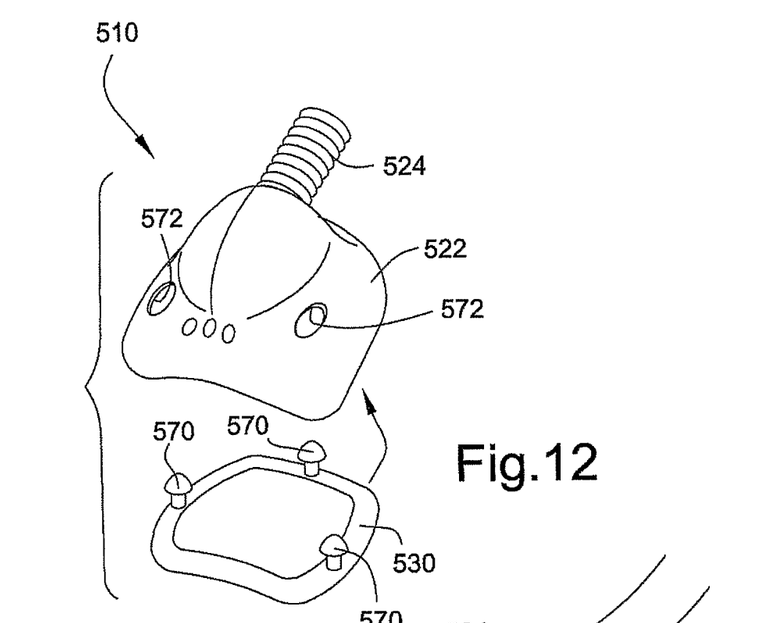
FIG. 12 is an exploded view of a nasal mask assembly according to another embodiment of the present invention.
Figure 13:
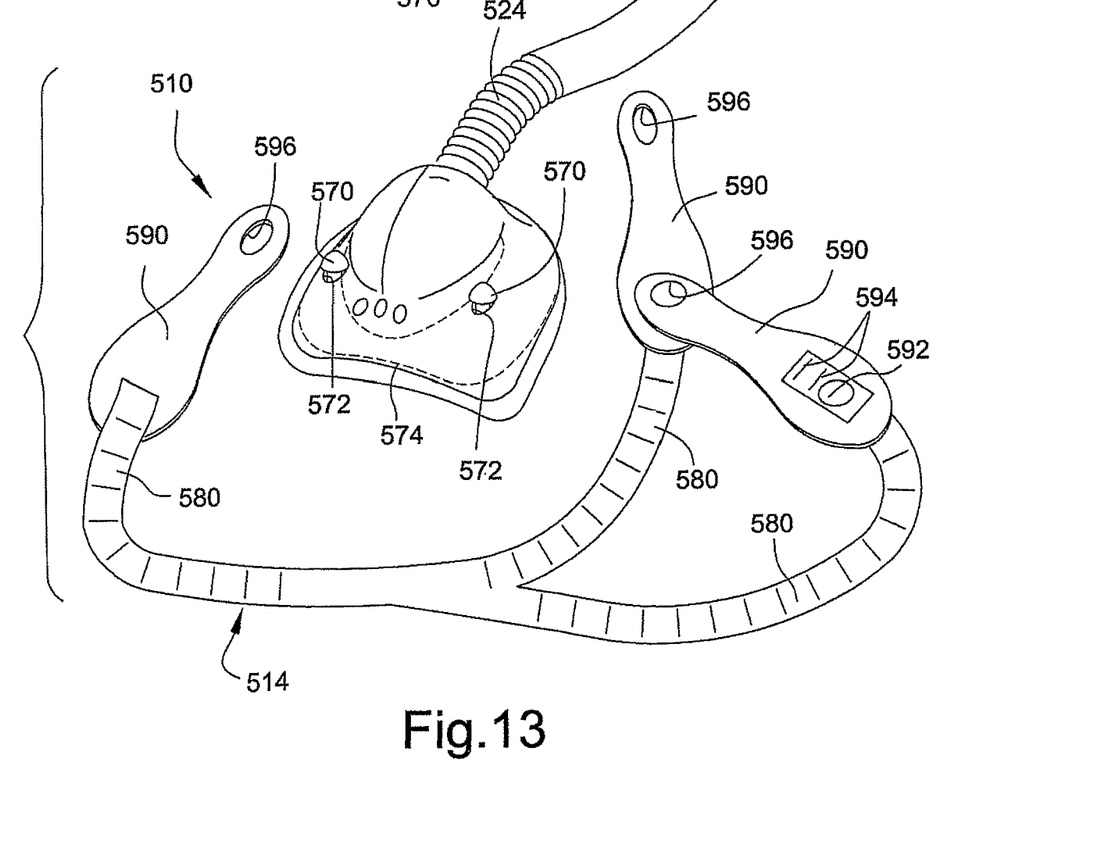
FIG. 13 is a perspective view of the nasal mask assembly shown in FIG. 12 in a partially assembled condition.

FIGS. 12 and 13 illustrate a nasal mask assembly 510 according to another embodiment of the present invention. As illustrated, the nasal mask assembly 510 includes a cushion 522 that provides a seal around the patient's nose, and a frame 530 and an air delivery tube 524 provided to the cushion 522. The frame 530 adds support or rigidity to the cushion 522 and provides attachment points for headgear.

Specifically, the frame 530 is generally ring-shaped and includes a plurality of attachment pins 570, e.g., three pins. The frame 530 attaches to the cushion 522 from below by inserting the pins 570 through respective openings 572 in the cushion 522 to attach the frame 530 to the cushion 522. Each pin 570 has an enlarged head to retain the pin 570 within the respective opening 572.

As illustrated in dashed lines, the cushion 522 has a support molding or pouch 574 at its interior to enclose the frame 530 when attached thereto. That is, the frame 530 is wrapped in the cushion's silicone material when attached so that the frame 530 will not contact patient's face in use.

The headgear 514 includes headgear straps 580 that are adapted to attach to the cushion 522 via the frame 530. Specifically, each headgear strap 580 includes an attachment member 590, e.g., formed of silicone. The attachment member 590 is adjustably mounted to the respective strap 580, e.g., by inserting pin 592 through a slot 594 provided in the strap 580, and includes an opening 596 adjacent the free end thereof. The attachment member 590 attaches to the cushion 522 by inserting the frame pin 570 (protruding through the cushion 522) through the opening 596.

3. Third Embodiment of Nasal Mask Assembly

Figure 14:
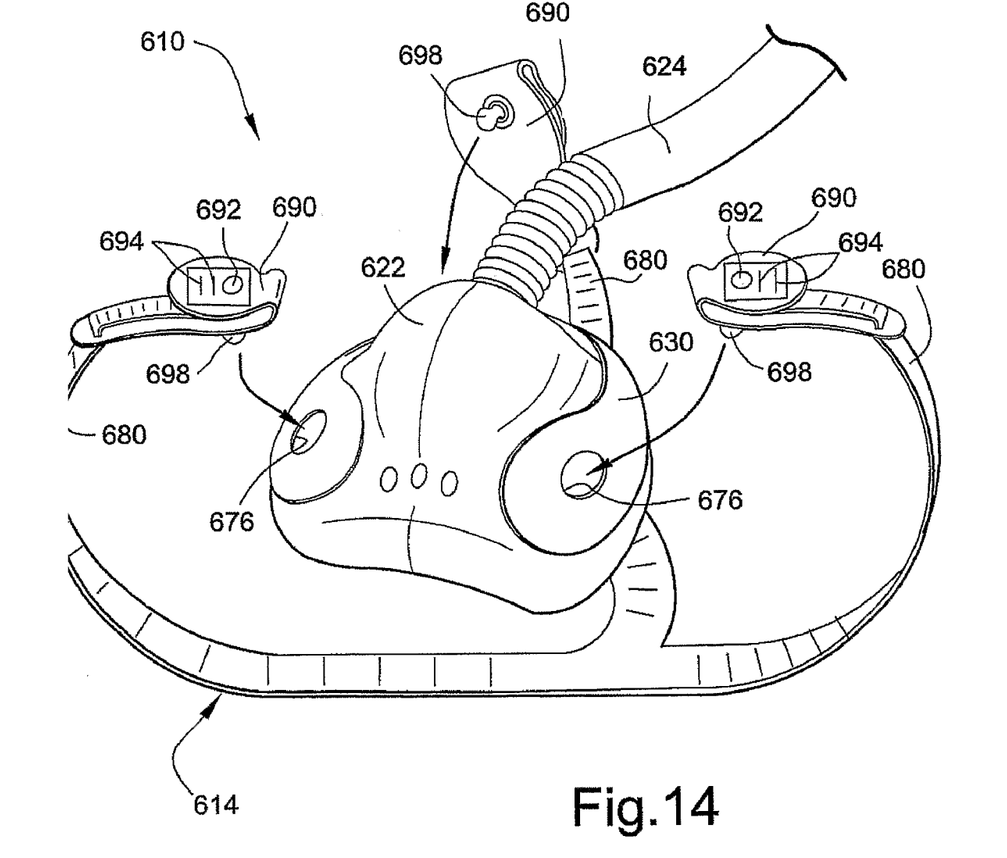
FIG. 14 is a perspective view of a nasal mask assembly according to another embodiment of the present invention.
Figure 15:
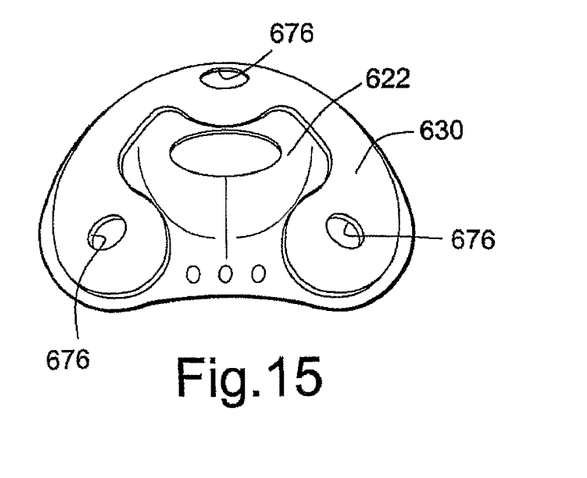
FIG. 15 is a top view of the nasal mask assembly shown in FIG. 14.

FIGS. 14 and 15 illustrate a nasal mask assembly 610 according to another embodiment of the present invention. As illustrated, the nasal mask assembly 610 includes a cushion 622 that provides a seal around the patient's nose, and a frame 630 and an air delivery tube 624 provided to the cushion 622. The frame 630 adds support or rigidity to the cushion 622 and provides attachment points for headgear.

Specifically, the frame 630, e.g., formed by molding, is generally U-shaped and wraps around the cushion exterior. The frame 630 may be secured to the cushion 630 in any suitable manner, e.g., mechanical interlock, adhesive, etc. The frame 630 includes a plurality of recesses 676, e.g., three recesses.

The headgear 614 includes headgear straps 680, e.g., formed of an elastic material, that are adapted to attach to the cushion 622 via the frame 630. Specifically, each headgear strap 680 includes an attachment member 690. The attachment member 690 is adjustably mounted to the respective strap 680, e.g., by inserting pin 692 through a slot 694 provided in the strap 680, and includes a pin 698 adjacent the free end thereof. The attachment member 690 attaches to the cushion 622 by engaging the pin 698 with a respective recess 676 provided to the frame 630, e.g., with a snap-fit, interference fit, etc.

4. Fourth Embodiment of Nasal Mask Assembly

Figure 16:
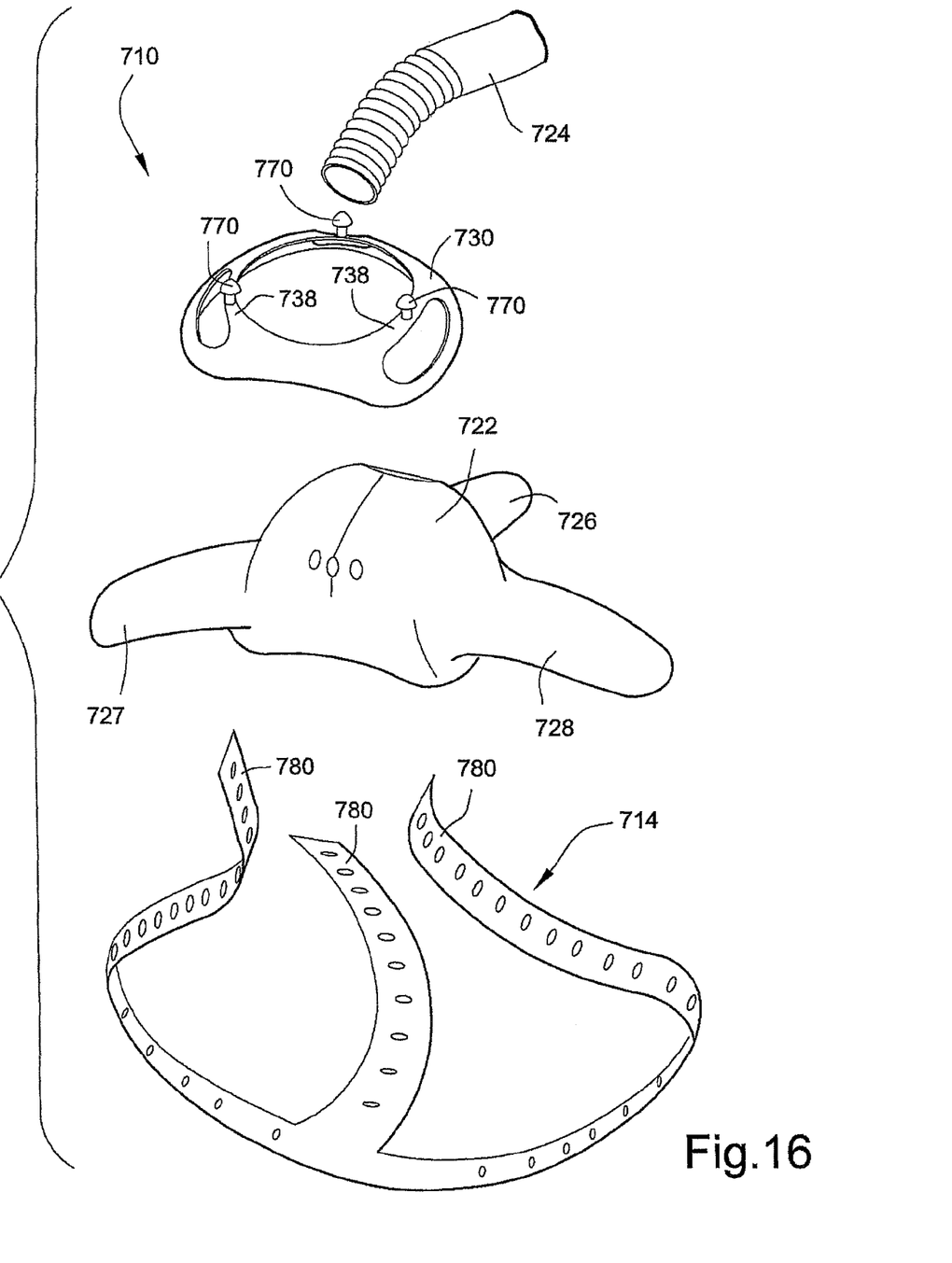
FIG. 16 is an exploded view of a nasal mask assembly according to another embodiment of the present invention.
Figure 17:
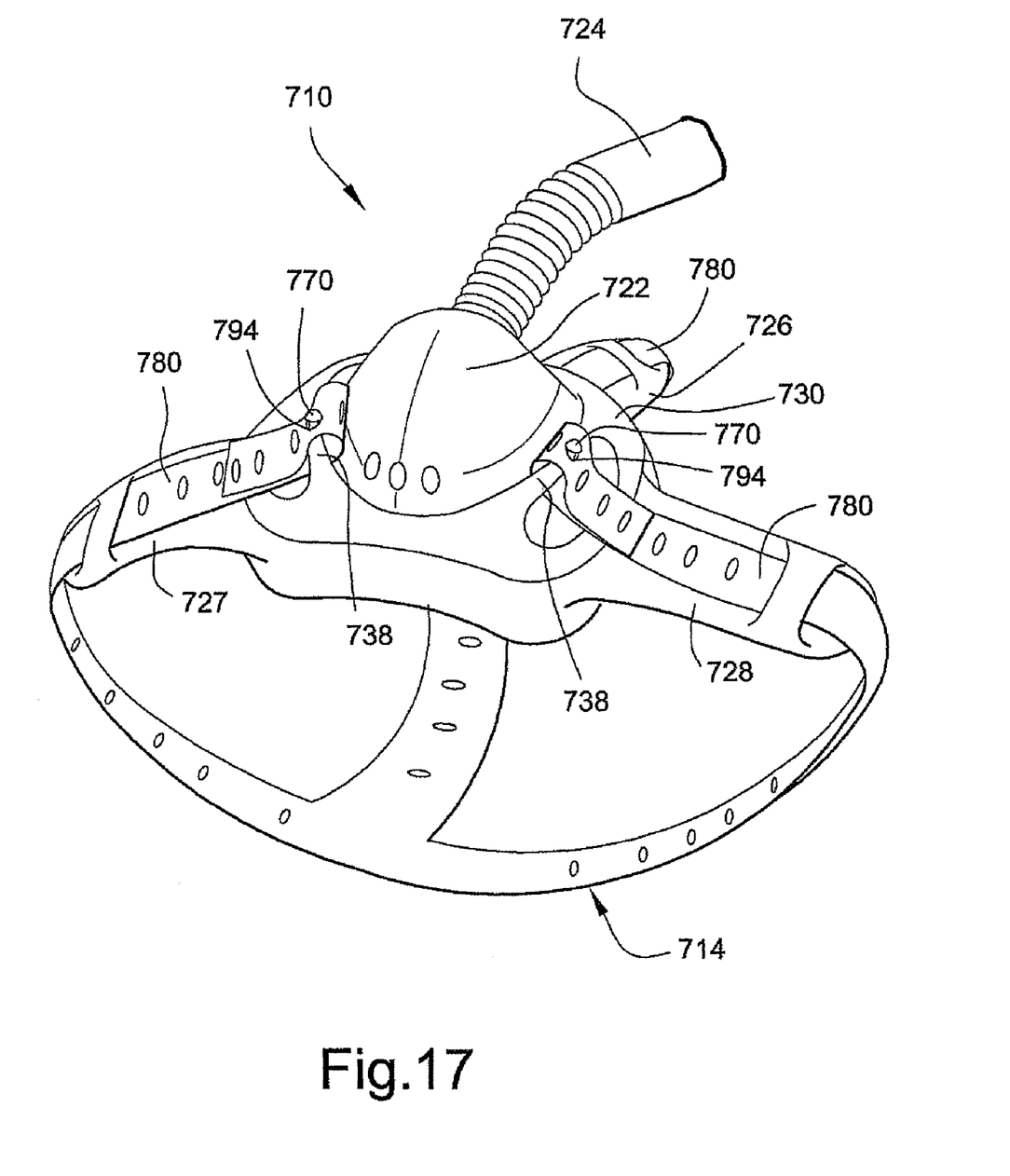
FIG. 17 is a perspective view of the nasal mask assembly shown in FIG. 16 in an assembled condition.

FIGS. 16 and 17 illustrate a nasal mask assembly 710 according to another embodiment of the present invention. As illustrated, the nasal mask assembly 710 includes a cushion 722 that provides a seal around the patient's nose, and a frame 730 and an air delivery tube 724 provided to the cushion 722. The frame 730 adds support or rigidity to the cushion 722 and provides attachment points for headgear.

Specifically, the frame 730, e.g., formed of bendable metallic or aluminum material, is generally ring-shaped and attaches to the cushion exterior. The frame 730 may be attached to the cushion 722 in any suitable manner, e.g., mechanical interlock, adhesive, etc. Also, the frame 730 may be bent to customize the shape of the cushion 722. As illustrated, the frame 730 defines a plurality of cross-bars or anchors 738, e.g., three cross-bars, each including an attachment pin 770.

The headgear 714 includes headgear straps 780, e.g., formed of an elastic material, that are adapted to attach to the cushion 722 via the frame 730. Specifically, each headgear strap 780 is wrapped around a respective cross-bar 738 of the frame 730. The strap 780 is secured in place by inserting the attachment pin 770 through a slot 794 provided in the strap 780.

Similar to the nasal mask assembly 10, the cushion 722 includes three support members or limbs 726, 727, 728 extending outwardly from the cushion 722. The support members 726, 727, 728 provide engagement points, e.g., loops, for engaging respective headgear straps 780. In use, the support members 726, 727, 728 support the cushion 722 on the patient's face and distribute forces to the cheeks and forehead of the patient.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A nasal mask assembly, comprising:
a relatively flexible cushion arrangement including a cushion that provides a breathing chamber and a face-contacting portion to form a seal around the patient's nose in use, an inlet tube supported by the cushion to deliver breathable gas into the breathing chamber for breathing by the patient, and three support members extending outwardly from the cushion;
a relatively rigid frame provided to a front side of the cushion arrangement, the frame including three headgear attachment structures; and
headgear including three headgear straps engagable with the three support members and the three headgear attachment structures to maintain the cushion arrangement in a desired position on the patient's face,
wherein the support members are arranged in a triangular configuration so that, in use, one of the support members extends over a patient forehead region and the other support members extend over a respective patent cheek region to evenly distribute a headgear force to the cushion, to the forehead region and to the respective cheek region on the patient's face.

2. The nasal mask assembly according to claim 1, wherein the cushion arrangement, frame, and headgear are sized and shaped for infants in the range of 6-18 months.

3. The nasal mask assembly according to claim 1, wherein the cushion arrangement is formed as a one-piece structure.

4. The nasal mask assembly according to claim 1, wherein the cushion arrangement is formed of silicone.

5. The nasal mask assembly according to claim 1, wherein the face contacting portion having a single wall construction.

6. The nasal mask assembly according to claim 1, wherein the cushion has a rounded trapezoidal shape.

7. The nasal mask assembly according to claim 1, wherein the cushion has a front wall that provides one or more vents for CO2 washout.

8. The nasal mask assembly according to claim 1, wherein the inlet tube is adapted to be connected to an air delivery tube, and the inlet tube curves upwardly so that the air delivery tube passes over the top of the patient's head in use.

9. The nasal mask assembly according to claim 1, wherein the inlet tube has an inside diameter of about 8 mm.

10. The nasal mask assembly according to claim 1, wherein each support member includes a loop that receives a respective headgear strap therethrough.

11. The nasal mask assembly according to claim 1, wherein the headgear straps pass over respective support members so that the headgear straps do not contact the patient's face in use.

12. The nasal mask assembly according to claim 1, wherein the support members evenly distribute the force of the cushion around the patient's face.

13. The nasal mask assembly according to claim 1, wherein an upper portion of the frame includes a recess and each side portion of the frame includes an anchor, and wherein one of the headgear straps may be passed through the recess and wrapped around the upper portion and the other headgear straps may be wrapped around respective anchors.

14. The nasal mask assembly according to claim 1, wherein the frame is provided to the front of the cushion arrangement so that the headgear straps can be adjusted at the front of the patient's face in use.

15. The nasal mask assembly according to claim 1, wherein the frame includes a cut-out to allow for one or more washout vents.

16. The nasal mask assembly according to claim 1, wherein the frame is bendable or malleable.

17. The nasal mask assembly according to claim 1, wherein each of the respective support members has a width that is wider than a width of the corresponding respective headgear strap.

18. The nasal mask assembly according to claim 1, wherein each of the support members are relatively flexible which allows the support members to bend or flex and match a contour of the patient's face in use.

19. The nasal mask assembly according to claim 1, wherein the support members are provided between the headgear straps and the patient's face in use to prevent contact of the headgear straps with the patient's face.

20. The nasal mask assembly according to claim 1, wherein each support member includes a limb extending outwardly from the cushion and a loop or anchor provided to an end of the limb to retain the respective headgear strap, the limb including a width that is sufficiently wider than a width of the loop or anchor.

21. The nasal mask assembly according to claim 1, wherein each of the support members include a width that is similar to a width of the cushion.

* * * * *